(12) United States Patent
Liu et al.

(10) Patent No.: US 7,742,244 B2
(45) Date of Patent: Jun. 22, 2010

(54) CYLINDRICAL MODEL EYE, CYLINDRICAL TEST DEVICE AND THE MANUFACTURING METHOD THEREOF

(75) Inventors: Wenli Liu, Beijing (CN); Jianping Zhu, Beijing (CN); Baoyu Hong, Beijing (CN); Fei Li, Beijing (CN); Zhenya Ma, Beijing (CN); Lei Yang, Beijing (CN)

(73) Assignee: National Institute of Metrology, Beijing (CN)

( * ) Notice: Subject to any disclaimer, the term of this patent is extended or adjusted under 35 U.S.C. 154(b) by 68 days.

(21) Appl. No.: 12/263,325

(22) Filed: Oct. 31, 2008

(65) Prior Publication Data
US 2009/0109434 A1    Apr. 30, 2009

(51) Int. Cl.
*G02B 9/00* (2006.01)
*A61B 3/10* (2006.01)

(52) U.S. Cl. ........................... 359/796; 351/205

(58) Field of Classification Search ............... 359/738, 359/794, 796, 798; 351/205, 212, 221, 246
See application file for complete search history.

(56) References Cited

U.S. PATENT DOCUMENTS

| 7,036,933 B2 * | 5/2006 | Yamaguchi et al. ......... 351/205 |
| 7,413,306 B2 * | 8/2008 | Campbell ..................... 351/233 |
| 2010/0002311 A1 * | 1/2010 | Reichert ..................... 359/738 |

* cited by examiner

*Primary Examiner*—Mohammed Hasan
(74) *Attorney, Agent, or Firm*—Finnegan, Henderson, Farabow, Garrett & Dunner, LLP

(57) ABSTRACT

A cylindrical model eye comprises a plano-cylindrical portion having a plano surface and a first cylindrical surface opposite to the plano surface, a sphero-cylindrical portion having a convex spherical surface and a second cylindrical surface opposite to the convex spherical surface. The second cylindrical surface mates with the first cylindrical surface, and the first cylindrical surface has substantially the same radius curvature radius as the second cylindrical surface.

17 Claims, 3 Drawing Sheets

CYLINDRICAL MODEL EYE, CYLINDRICAL TEST DEVICE AND THE MANUFACTURING METHOD THEREOF

BACKGROUND OF THE INVENTION

1. Field of the Invention

This application claims the benefit of Chinese Patent Application No. 200710176603.7, filed Oct. 31, 2007, which is incorporated by reference herein.

The present invention relates to the field of test methods for eye refractometers using an objective measuring principle. More specifically, the present invention relates to a cylindrical model eye, a cylindrical test device and the manufacturing method thereof. The cylindrical test device is mainly used for testing the cylindrical vertex power and cylinder axis accuracy of eye refractometers.

2. Description of the Related Art

Dioptre inspection, also called optometry, means examination of an eye's refractive errors for a patient by a series of inspections. The device used for optometry is called an eye refractometer. The eye refractometer primarily measures the spherical vertex power (myopia or hyperopia), the cylindrical vertex power (astigmatism) and cylinder axis (i.e. axis of astigmatism) etc. of the eye.

Corresponding test devices have to be used for testing eye refractometers, to check data therefrom for accuracy and reliability. The test device for testing the spherical vertex power of an eye refractometer is called as a spherical model eye, and the test device for testing the cylindrical vertex power and cylinder axis of the eye refractometer is called as a cylindrical test device.

The spherical model eye, recommended in ISO 10342 "Eye refractometers", is made of optical glass and is formed with a spherical front surface and a lightly frosted plano back surface. The spherical model eye is easy to be manufactured easily because that the processing technique for optical components with spherical surfaces is advanced.

As to the cylindrical test device, two solutions are recommended in ISO 10342 "Eye refractometers". One solution is a model eye with a front toric surface. Another is addition of a thin rigid toric lens with an 8 mm base curve to the spherical model eye.

A first solution is a modification of the spherical model eye. It uses a toric surface instead of the spherical surface as the front surface.

The toric surface is a surface for which two main principal curvatures are unequal a lens with a toric surface will bring paraxial parallel light to two separate line foci mutually at right angles, hence having different vertex powers in two meridian planes. The cylindrical vertex power is defined as the difference between the two vertex powers in the two meridian planes.

In order to meet the requirements in ISO 10342 "Eye refractometers", such a toric surface cylindrical model eye is made of optical glass. Furthermore, the curvature radii of the two main meridian planes are both nearly about 8 mm, and the manufacture thereof is difficult.

The second solution is advantageous because it is easy to manufacture the spherical model eye. However, it is difficult to manufacture a thin rigid toric lens with an 8 mm base curve. Experimentation with addition of well-known astigmatic contact lenses, to the spherical model eye has been done. The experiment shows the following disadvantages.

If a soft astigmatic contact lens is added to the spherical model eye, due to variable water content of the soft astigmatic contact lens, the shape and the dimensions thereof vary continuously, thus, the cylindrical vertex power and the cylinder axis of the combination of the soft astigmatic contact lens and the spherical model eye are unstable.

If a hard astigmatic contact lens is added to the spherical model eye, it is difficult to solve the coaxial and concentric problems after assembly due to the different design parameters and the limited manufacture capability of the hard astigmatic contact lens, and the testing results are influenced by the problems such as ghost image when the refractometer is detected.

Therefore, the practicability and reliability of the two conventional solutions is inadequate.

SUMMARY

In view of the above disadvantages in the conventional art, the present invention provides a cylindrical model eye combining a sphero-cylindrical portion with a plano-cylindrical portion, which not only reduces manufacturing difficulty and cost, but also shows good practicability for testing the cylindrical vertex power and in cylinder axis accuracy of eye refractometers.

According to the preferred embodiment of the invention, a cylindrical model eye, comprising: a plano-cylindrical portion which at least is formed with a plano surface and a first cylindrical surface opposite the plano surface; a sphero-cylindrical portion which is formed with a convex spherical surface and a second cylindrical surface opposing to the convex spherical surface; wherein the shape of the second cylindrical surface is mate with that of the first cylindrical surface, and the second cylindrical surface has the same curvature radius as that of the first cylindrical surface.

According to the preferred embodiment of the invention, the plano surface is a frosted surface. And the plano surface is coated with brown coating material to imitate a yellow spot of a human eye. The second cylindrical surface is bonded with the first cylindrical surface by transparent adhesive.

According to the preferred embodiment of the invention, the plano-cylindrical portion and the sphero-cylindrical portion are made of achromatic optical materials with different refractive indexes but the same Abbe numbers. The bonded surface is a cylindrical surface, and the different refractive indexes of the two portions makes the cylindrical model eye have different vertex powers in the meridian planes, hence achieving the cylindrical power.

According to the preferred embodiment of the invention, the plano-cylindrical portion further comprises an axis positioning portion between the plano surface and the first cylindrical surface to position the cylinder axis of the cylindrical model eye. The axis positioning portion has a rectangular cylindrical shape. Thus, as a testing requirement, a cylindrical model eye with a cylinder axis of 0(180) degrees and a cylindrical model eye with a cylinder axis of 90 degrees can be provided at the same time.

According to the preferred embodiment of the invention, a cylindrical test device for testing eye refractometers is provided, the cylindrical test device including the cylindrical model eye as described above, and an axis holder for holding the cylindrical model eye.

In the above cylindrical test device, the axis holder is formed with at least a through hole for receiving the model eye.

In the cylindrical test device, the through hole is a rectangular through hole, and there are two through holes for receiving a pair of the cylindrical model eyes respectively.

In the cylindrical test device, both ends of the rectangular through holes in the axis holder are provided with cylindrical thread structures, and the cylindrical test device further comprises: a diaphragm provided in front of the convex spherical surface of the cylindrical model eye; a first clamping ring, formed with threads thereon, provided outside of the diaphragm to engage one of the cylindrical thread structures; and a second clamping ring, formed with threads thereon, provided outside of the plano surface of the cylindrical model eye to engage with another one of the cylindrical thread structures.

According to another aspect of the invention, a method for manufacturing a cylindrical model eye is provided, including forming a plano-cylindrical portion which at least is formed with a plano surface and a first cylindrical surface opposing to the plano surface; forming a sphero-cylindrical portion which is formed with a convex spherical surface and a second cylindrical surface opposing to the convex spherical surface; bonding the plano-cylindrical portion with the sphero-cylindrical portion, wherein the shape of the second cylindrical surface is mated with that of the first cylindrical surface, and the second cylindrical surface has the same curvature radius with that of the first cylindrical surface.

According to a further aspect of the invention, a method for manufacturing a cylindrical test device for testing eye refractometers, including providing a cylindrical model eye as manufactured by the method for manufacturing a cylindrical model eye as described above; and providing an axis holder for holding the cylindrical model eye.

In the present invention, since the cylindrical model eye is combined by a plano-cylindrical portion with a sphero-cylindrical portion, the second cylindrical surface of the sphero-cylindrical portion is mated with the first cylindrical surface of the plano-cylindrical portion and the second cylindrical surface has the same curvature radius with that of the first cylindrical surface, increasing of cost due to manufacturing difficulty in prior art is solved. And the cylindrical vertex power indication error and the cylinder axis indication error of eye refractometer can be accurately measured.

BRIEF DESCRIPTION OF THE DRAWINGS

Further disclosure, objects, advantages and aspects of the present invention may be better understood by those skilled in the relevant art by reference to the following description of embodiments taken in conjunction with the accompanying drawings, which are given by way of illustration only, and thus do not limit the scope of the present invention.

DETAILED DESCRIPTION OF THE PREFERRED EMBODIMENTS

Figure 1:
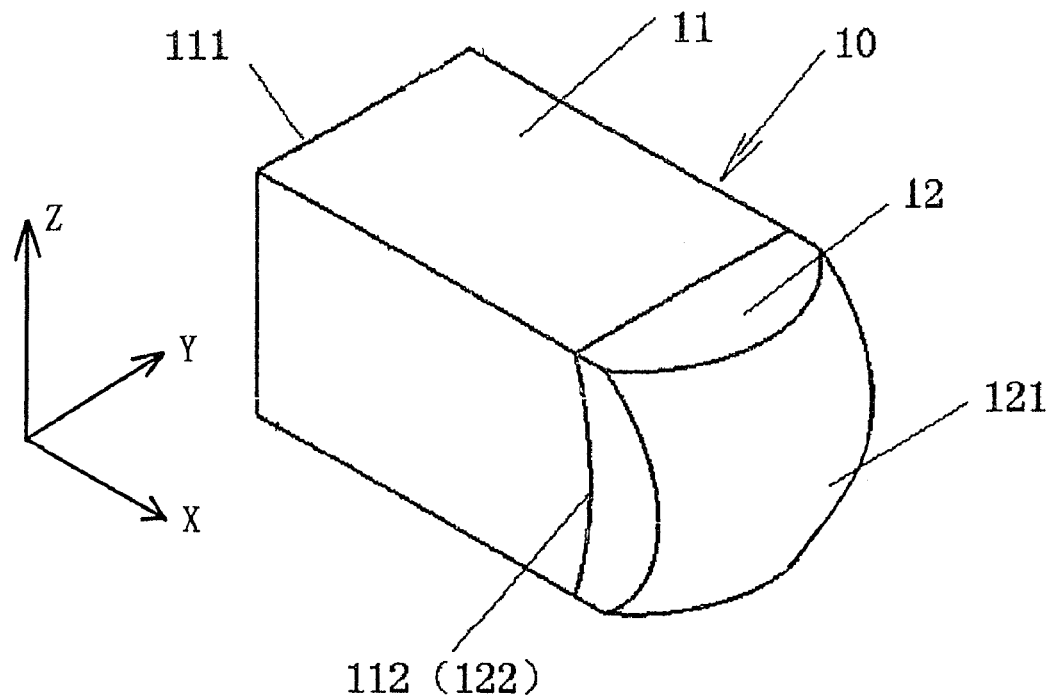
FIG. 1 is a perspective view of a cylindrical model eye according to a preferred embodiment of the invention.

Above and other aspects of features of the present invention will be readily apparent in view of the below detailed discussion of preferred embodiments and references to accompanying drawings, wherein like reference numerals refer to like elements throughout the specification.

In a preferred embodiment of the invention, a cylindrical test device 100 for testing eye refractometers will be described in detail. The cylindrical test device comprises a cylindrical model eye 10 and an axis holder 20. The cylindrical test device is used for testing cylindrical vertex power and cylinder axis accuracy of eye refractometers.

Figure 4A:
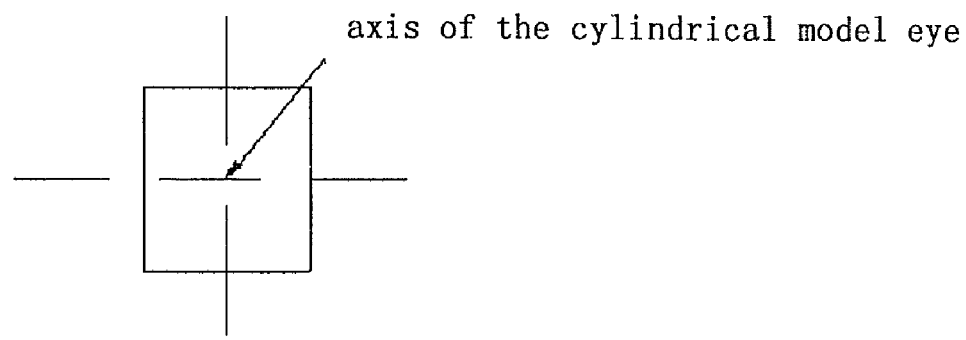
FIGS. 4a, 4b and 4c are plan views of a cylindrical model eye according to a preferred embodiment of the invention shown in FIG. 1 as seen from directions X, Y and Z, respectively.
Figure 4B:
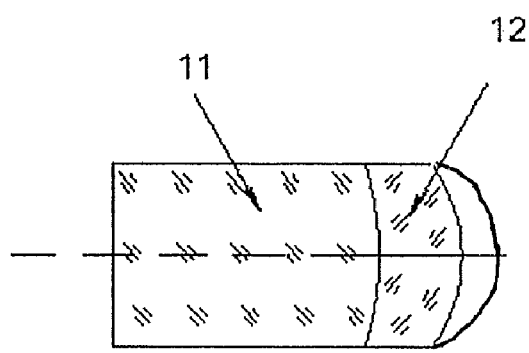
Figure 4C:
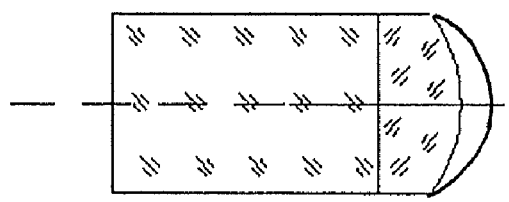

More specifically, according to a preferred embodiment of the invention, a cylindrical standard test device 100, comprises a cylindrical model eye 10, as broadly embodied in FIG. 1, which is a substantially parallelepiped cylindrical body with two segments, i.e., the cylindrical model eye 10 comprises a plano-cylindrical portion 11 and a sphero-cylindrical portion 12. As shown in FIGS. 4a, 4b and 4c, a first end face of the plano-cylindrical portion 11 is a plano surface 111, and a second end face of the plano-cylindrical portion 11 opposite the first end face is a first cylindrical surface 112. A first end face of the sphero-cylindrical portion 12 is a second cylindrical surface 122, and a second end face of the sphero-cylindrical portion 12 opposite to the first end face is a convex spherical surface 121. The second cylindrical surface 122 is mated with the first cylindrical surface 112, and the second cylindrical surface 122 has the same radius of curvature with that of the first cylindrical surface 112, so that the plano-cylindrical portion 11 and the sphero-cylindrical portion 12 can be fitted together by bonding the second cylindrical surface 122 with the first cylindrical surface 112. In the preferred embodiment of the invention, the first cylindrical surface 112 is convex, and the second cylindrical surface 122 is concave. However, it will be appreciated by those skilled in the art that the present invention is not limited thereto as long as the shape of the second cylindrical surface 122 and the first cylindrical surface 112 is mated together. Further, the second cylindrical surface 122 and the first cylindrical surface 112 preferably are bonded by transparent adhesive.

Figure 2:
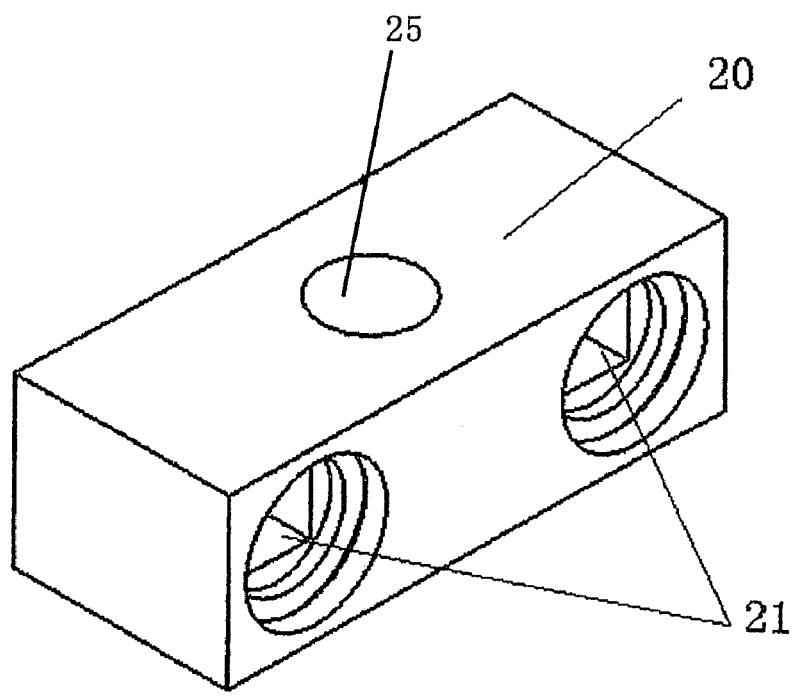
FIG. 2 is a perspective view of an axis holder according to a preferred embodiment of the invention.

The cylindrical test device 100 further comprises an axis holder 20 (FIG. 2) for holding the cylindrical model eye 10. In the preferred embodiment of the invention, the outer shape of the axis holder 20 can be formed as a rectangular parallelepiped body, and two rectangular through holes 21 are defined at predetermined intervals on the axis holder 20. Alternatively, the axis holder 20 can be provided with only one through hole 21. A circular through hole 25, of which the axis is perpendicular to those of the two square through holes 21, is formed at substantially intermediate the two opposing surfaces of the axis holder 20 for connecting the cylindrical test device 100 with an eye refractometer during testing as broadly embodied in FIG. 3, the cylindrical model eye 10 is provided in the through holes 21 of the axis holder 20. In a further preferred embodiment of the invention, cylindrical portions are provided at both ends of the through holes 21 of the axis holder 20, and threads are formed thereon. After the cylindrical model eye 10 is put into the through holes 21, a diagram 22 is provided in front of the convex spherical surface 121 of the cylindrical model eye 10, then fixed by a pressing ring 23 with threads formed on a peripheral ring thereof, as broadly embodied in FIG. 3, the end of the plano surface 111 of the cylindrical model eye 10 is fixed by a pressing ring 24 with threads formed on peripheral ring as well.

The plano-cylindrical portion 11 and the sphero-cylindrical portion 12 of the cylindrical model eye 10 preferably are made of achromatic optical materials, such as glass, plastic, crystal, or the like, with substantially similar Abbe numbers and different refractive indexes.

In the preferred embodiment of the invention, the plano surface 111 of the plano-cylindrical portion 11 is frosted to imitate the retina of human eye. The convex spherical surface 121 of the sphero-cylindrical portion 12 preferably is polished to imitate the cornea of human eye. The first cylindrical surface 112 of the plano-cylindrical portion 11 and the second cylindrical surface 122 of the spherical cylindrical portion 12 adhere to each other to form a complete cylindrical model eye 10. The adhesive used here has to be firm and reliable enough not to influence the image quality of the cylindrical lens model eye, with the refractive index of the adhesive being preferably between 1.53 and 1.60. A person normally skilled in the art, however, will recognize that the second cylindrical surface and the first cylindrical surface can be bonded together by any known means, such as fusion etc. In the preferred embodiment of the invention, brown coating material is coated on the frosted plano surface 111 to imitate a yellow spot of the human eye.

The plano-cylindrical portion 11 and the sphero-cylindrical portion 12 are both made of achromatic optical materials with substantially similar Abbe numbers, i.e., dispersion coefficients, and different refractive indexes. The two portions 11 and 12 have different refractive indexes, and the adhered surface being a cylindrical surface, defines a cylindrical model eye having different vertex powers in two meridian planes and hence achieves the cylinder power. The meridian vertex powers are determined by the curvature radii of the convex spherical surface 121, the first cylindrical surface 112 and the second cylindrical surface 122, the central thickness of the plano-cylindrical portion 11, the total length of the cylindrical model eye 10, the material refractive indexes. So a cylindrical model eye 10 with requested spherical power and cylinder power, for example with spherical power of $0 \ m^{-1}$ and cylindrical power of $-3 \ m^{-1}$, can be obtained by selecting suitable values for the above parameters, so that the cylindrical vertex power indication error of eye refractometer can be tested.

For axis-positioning purposes, the cylindrical model eye 10 is formed with an axis positioning portion. In the preferred embodiment of the invention, the axis positioning portion is formed by forming the cylindrical model eye 10 about the shape of a rectangular cylinder. A person of normal in the art will recognize that other shapes will achieve the axis positioning structure of the cylindrical model eye 10 only if the cylindrical model eye 10 can not be rotated in the through hole while receiving therein. For example, the cylindrical model eye 10 can be formed with one plane or two perpendicular planes to position the cylindrical model eye 10 in the axis holder 20. Similarly, the axis holder 20 can be formed with receiving grooves for engaging with the one plane or with both perpendicular planes. Forming the cylindrical model eye 10 was a rectangular parallelepiped structure is illustrative rather than limiting.

In the preferred embodiment of the cylindrical model eye 10, the shape thereof is a rectangular cylinder with a face thereof provided as a reference plane. The cylinder axis direction of the cylindrical model eye is parallel to the reference plane. This design ensures that cylinder axis directions of 0(180) degree and 90 degree can be obtained after the cylindrical model eye 10 is inserted into the axis holder 20. Meanwhile, for convenience of assembly, the four edges of the cylindrical model eye 10 can be chamfered. Alternatively, other cylinder axis directions of 45 degrees, 135 degrees, 60 degrees, and 150 degrees or the like, can be obtained after the cylindrical model eye 10 is inserted into the axis holder 20.

In the preferred embodiment of the invention, since the axis holder is provided with rectangular through holes 21, the accurate positioning of cylinder axis directions of 0(180) degrees and 90 degrees can be solved by engaging the rectangular through hole 21 with the axial positioning portion of the cylindrical model eye 10. In the present invention, the axial positioning portion is formed by forming the cylindrical model eye 10 to have a rectangular cylinder shape. Alternatively, the through hole 21 and the cylindrical model eye 10 may be formed into other shapes, such as, cylindrical shapes, as long as they can be mated with each other in shapes. In addition, by strictly controlling the central distance between the two square through holes 21, the pupil distance measuring error of eye refractometer can also be tested.

Figure 3:
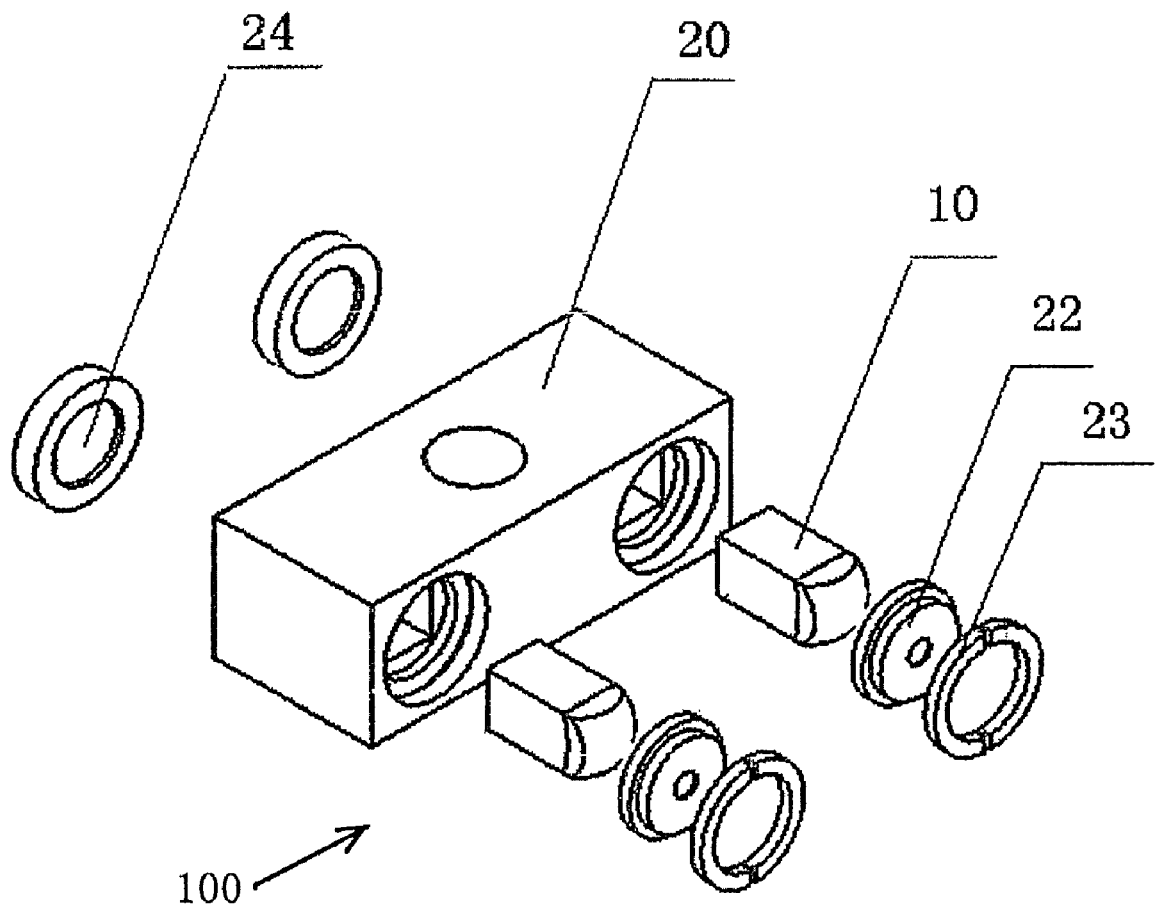
FIG. 3 is an exploded perspective view of a cylindrical test device assembled by the cylindrical model eye and the axis holder in FIGS. 1 and 2.

FIG. 3 broadly depicts an assembled view of the cylindrical test device according to the invention. The aforementioned cylindrical model eye 10 and the axis holder 20 are assembled into a complete cylindrical test device by the strict assembly positioning procedure according to the present invention.

As shown in the figures, in an exemplary embodiment of the present invention, two cylindrical model eyes 10 are assembled into the through holes 21 of the axis holder 20. Meanwhile, it should be ensured during assembly that the reference plane of one cylindrical model eye should be overlapped or parallel to that of the axis holder 20 whereas the reference plane of the other cylindrical model eye 10 is perpendicular to that of the axis holder, thus achieving the required cylinder axis directions of 0(180) degree and 90 degree, and the cylinder axis indication error of eye refractometer can be tested.

In a further preferred embodiment of the invention, the plano surface 111 of the cylindrical model eye 10 is fixed by the pressing ring 24 with threads formed on peripheral ring. The diaphragm 22 is provided in front of the convex spherical surface 121 of the cylindrical model eye 10, and is fixed by the pressing ring 23 with threads formed on peripheral ring as well. The aperture radius of the diaphragm 22 is about 4 mm so as to imitate the pupil of human eye, and it can reduce an influence of stray light to the testing results.

Manufacturing methods for the cylindrical model eye and the cylindrical test device according to the invention are described below.

The method for manufacturing a cylindrical model eye according to a preferred embodiment of the invention comprises the following steps. A plano-cylindrical portion 11 is formed, which includes at least a plano surface 111 and a first cylindrical surface 112 opposite to the plano surface 111. A sphero-cylindrical portion is formed, opposite with a convex spherical surface 121 and a second cylindrical surface 122 opposite the convex spherical surface 121. The plano-cylindrical portion 11 is engaged with the sphero-cylindrical portion 12, with the shapes of the first cylindrical surface 112 and the second cylindrical surface 122 mating with each other, and the second cylindrical surface 122 and the first cylindrical surface 112 having the same curvature radiuses. The plano-cylindrical portion 11 and the sphero-cylindrical portion 12 are made of achromatic optical materials with different refractive indexes and the substantially similar Abbe numbers. The plano surface 111 of the plano-cylindrical portion 11 is frosted and coated with brown coating material to imitate the yellow spot of the human eye.

According to the preferred embodiment of the invention, a method for manufacturing a cylindrical test device 100 for testing eye refractometers is provided, comprising: providing a cylindrical model eye 10 as manufactured by the method mentioned above; and providing an axis holder 20 for holding the cylindrical model eye 10. In order to hold the cylindrical model eye 10 in the axis holder 20, rectangular through holes 21 are formed on the axis holder 20 which are spaced apart as presented intervals on the two opposing faces of the axis holder 20. In addition, by controlling the central distance of the two rectangular through holes 21, the pupil distance of human eye can be simulated.

It should be noted that, in the cylindrical model eye, the cylindrical test device and the manufacturing methods thereof, the second cylindrical surface has the same curvature radius as that of the first cylindrical surface, thereby preventing an increase in cost due to the manufacturing difficulty of the toric processing. In addition, the unique design of the axis holder and the positioning of cylinder axis directions of 0(180) degrees and 90 degrees is accurately achieved by engaging the rectangular through holes with the square cylindrical model eyes. Thus, cylindrical vertex power and cylinder axis indication errors of eye refractometer can be accurately measured.

While the embodiments of the present invention have been described by way of examples taken in conjunction with the accompanying drawings, it should be appreciated that modifications, additions and variations to and from the above described embodiments may be made without deviating from the scope of the present invention which is defined by the accompanying claims and their equivalents.

What is claimed is:

1. A model eye, comprising:
   a plano-cylindrical portion having a plano surface and a first cylindrical surface opposite to the plano surface; and
   a sphero-cylindrical portion having a convex spherical surface and a second cylindrical surface opposite to the convex spherical surface;
   wherein the second cylindrical surface mates with the first cylindrical surface, and the first cylindrical surface has a first radius of curvature which is substantially identical to a second radius of curvature of the second cylindrical surface.

2. The cylindrical model eye according to claim 1, wherein the plano-cylindrical portion and the sphero-cylindrical portion comprise achromatic optical materials with different refractive indexes, and substantially similar Abbe numbers.

3. The cylindrical model eye according to claim 1, wherein the plano surface is a frosted surface.

4. The cylindrical model eye according to claim 3, wherein the plano surface is coated with a coating material.

5. The cylindrical model eye according to claim 1, wherein the first cylindrical surface is bonded to the second cylindrical surface with a substantially transparent adhesive.

6. The cylindrical model eye according to claim 1, wherein the plano-cylindrical portion further comprises an axis positioning portion between the plano surface and the first cylindrical surface for positioning a cylindrical axis of the cylindrical model eye.

7. The cylindrical model eye according to claim 6, wherein the axis positioning portion has a rectangular cylindrical shape.

8. A cylindrical test device for testing eye refractometers, the cylindrical test device comprising:
   the cylindrical model eye according to claim 1; and
   an axis holder for holding the cylindrical model eye.

9. The cylindrical test device according to claim 8, wherein the axis holder is formed with a through hole for receiving the model eye.

10. The cylindrical test device according to claim 9, further comprising a second through hole wherein the through holes are rectangular through holes for receiving a pair of the cylindrical model eyes respectively.

11. The cylindrical test device according to claim 10, further comprising:
    cylindrical thread structures on ends of the rectangular through holes;
    a diaphragm provided in front of a convex spherical surface of the cylindrical model eye;
    a first clamping ring, formed with threads thereon, provided outside of the diaphragm to engage with one of the cylindrical thread structures; and
    a second clamping ring, formed with threads thereon, provided outside of the plano surface of the cylindrical model eye to engage with another one of the cylindrical thread structures.

12. The cylindrical test device according to claim 10, wherein the two cylindrical model eyes are provided to have a cylinder axis of 0(180) degrees and a cylinder axis of 90 degrees respectively.

13. A method for manufacturing a cylindrical model eye, comprising:
    forming a plano-cylindrical portion having a plano surface and a first cylindrical surface opposite to the plano surface;
    forming a sphero-cylindrical portion having a convex spherical surface and a second cylindrical surface opposite to the convex spherical surface;
    bonding the plano-cylindrical portion with the sphero-cylindrical portion, wherein the second cylindrical surface mates with the first cylindrical surface, and the first cylindrical surface has a first radius curvature of the second cylindrical surface.

14. The method for manufacturing a cylindrical model eye according to claim 13, wherein the plano-cylindrical portion and the sphero-cylindrical portion comprise of achromatic optical materials having different refractive indexes and substantially similar Abbe numbers.

15. The method for manufacturing a cylindrical model eye according to claim 13, further comprising frosting the plano surface.

16. The method for manufacturing a cylindrical model eye according to claim 15, wherein the plano surface is coated with a coating material.

17. The method for manufacturing a cylindrical model eye according to claim 13, wherein the second cylindrical surface is bonded to the first cylindrical surface by a substantially transparent adhesive.

* * * * *

UNITED STATES PATENT AND TRADEMARK OFFICE
CERTIFICATE OF CORRECTION

PATENT NO. : 7,742,244 B2  
APPLICATION NO. : 12/263325  
DATED : June 22, 2010  
INVENTOR(S) : Wenli Liu et al.

Page 1 of 1

It is certified that error appears in the above-identified patent and that said Letters Patent is hereby corrected as shown below:

On the Title Page, after Item (65), the "Prior Publication Data", and before Item (51), the "Int. Cl." data, insert the following missing data:
--(30)    Foreign Application Priority Data
    Oct. 31, 2007    (CN) .......... 200710176603--.

Signed and Sealed this

Sixteenth Day of November, 2010

David J. Kappos  
*Director of the United States Patent and Trademark Office*